United States Patent
Balay et al.

(10) Patent No.: US 6,231,612 B1
(45) Date of Patent: May 15, 2001

(54) ACETABULAR IMPLANT FIXED WITHOUT CEMENT

(76) Inventors: Bruno Balay, 70 Chemin des Erables 01600, Saint Bernard; Jean Claude Cartillier, 56 rue du Professeur P. Sisley 69008, Lyons; Claude Charlet, 77 Chemin des Esses 69370, Saint Didier au Mont d'Or; Alain Machenaud, 8 rue de l'Isernon 74000, Cran Gevrier; Jean Marc Semay, 13 rue Beaumont 42270, Saint Priest en Jarest; Louis Setiey, La Rippe 69400, Gleize; Jean Pierre Vidalain, La Boisserie 8 rue du Pont de Thé 74000, Annecy le Vieux, all of (FR)

( * ) Notice: Subject to any disclaimer, the term of this patent is extended or adjusted under 35 U.S.C. 154(b) by 0 days.

(21) Appl. No.: 08/983,465

(22) PCT Filed: May 14, 1997

(86) PCT No.: PCT/FR97/00860

§ 371 Date: May 4, 1998

§ 102(e) Date: May 4, 1998

(87) PCT Pub. No.: WO97/42913

PCT Pub. Date: Nov. 20, 1997

(30) Foreign Application Priority Data

May 14, 1996 (FR) .................................................. 96 06243
May 14, 1996 (FR) .................................................. 96 06244

(51) Int. Cl.$^7$ ....................................................... A61F 2/32
(52) U.S. Cl. ..................................... 623/22.31; 623/22.38
(58) Field of Search ................................ 623/22, 23, 16, 623/22.11, 22.12, 22.13, 22.15, 22.16, 22.17, 22.18, 22.19, 22.2, 22.21, 22.22, 22.23, 22.24, 22.25, 22.27, 22.31, 22.33, 22.32, 22.38, 22.39, 19.12, 19.13, 23.4, 23.43, 23.5

(56) References Cited

U.S. PATENT DOCUMENTS

| 4,892,549 | * | 1/1990 | Figgie, III et al. | 623/22 |
| 5,358,532 | * | 10/1994 | Evans et al. | 623/22 |
| 5,458,650 | * | 10/1995 | Carret et al. | 623/22 |
| 5,571,201 | * | 11/1996 | Averill et al. | 623/22 |
| 5,755,799 | * | 5/1998 | Oehy et al. | 623/18 |

FOREIGN PATENT DOCUMENTS

| 149975 | | 7/1985 | (DE) . | |
| 4337936 | | 5/1995 | (DE) . | |
| 4408527 | | 9/1995 | (DE) . | |
| 245527 | * | 5/1986 | (EP) | 623/22 |
| 245527 | | 11/1987 | (EP) . | |
| 169978 | | 1/1989 | (EP) . | |
| 341198 | | 11/1989 | (EP) . | |
| 444381 | * | 12/1990 | (EP) | 623/22 |

(List continued on next page.)

Primary Examiner—David H. Willse
Assistant Examiner—Alvin Stewart
(74) Attorney, Agent, or Firm—Sughrue, Mion, Zinn, Macpeak & Seas, PLLC

(57) ABSTRACT

The cotyloidal implant has a hemispherical cup (5) forming an internal cavity (10), and an insert (7) engageable into the cavity, the cup being set in place by impaction and having to this effect anchoring asperities (15) provided on its external face, having the form of lozenges and which are contiguous and imbricated. The cup (5) is provided, on its external face, with two coaxial grooves configured like helical threads (38) having reverse pitches which intersect each other on a large portion of said external face, which are inclined in the direction of the cup opening and which have a depth increasing progressively in the opening direction of the cup (5); due to their intersection, the grooves delimit an important number of asperities (15). The invention provides for the making of a cotyloidal implant which can be anchored to the pelvis without the use of cement and screws.

12 Claims, 1 Drawing Sheet

FOREIGN PATENT DOCUMENTS

| | | |
|---|---|---|
| 407332 | 1/1991 | (EP) . |
| 444381 | 9/1991 | (EP) . |
| 485678 | 5/1992 | (EP) . |
| 499475 | 8/1992 | (EP) . |
| 677280 * | 11/1994 | (EP) ...................................... 623/22 |
| 677280 | 10/1995 | (EP) . |
| 2519248 * | 7/1983 | (FR) ...................................... 623/22 |
| 2592787 * | 7/1987 | (FR) ...................................... 623/22 |
| 2630907 * | 5/1988 | (FR) ...................................... 623/22 |
| 2630907 | 11/1989 | (FR) . |
| 2660546 | 4/1990 | (FR) . |
| 2638963 | 5/1990 | (FR) . |
| 2678510 | 7/1991 | (FR) . |
| 2268408 | 1/1994 | (GB) . |
| 9405234 * | 3/1994 | (WO) ...................................... 623/22 |
| WO 95/22944 | 8/1995 | (WO) . |

* cited by examiner

ACETABULAR IMPLANT FIXED WITHOUT CEMENT

BACKGROUND OF THE INVENTION

The present invention relates to an acetabular implant attached without cement.

An acetabular implant usually comprises a cup of hemispherical shape, delimiting an interior cavity, and an insert that can be fitted into this cavity. The cup is intended to be fitted into the acetabular cavity and to be attached to the pelvis, and the insert delimits a spherical cavity intended to accommodate, with a possibility of pivoting, the corresponding spherical head of a femoral shaft.

The cup is generally made of a metal, especially titanium, and the insert is made of a material which encourages the head of the femur to slide, for example an alumina ceramic or a high-density polyethylene.

Some implants are attached to the innominate bone using polymerizable synthetic cement; others are attached without cement using mechanical anchoring means such as screws.

Among these, there are so-called "press-fit" implants which are intended to be inserted forcibly into the acetabular cavity. The cup of an implant of this kind has an outside diameter which is slightly larger than that of the acetabular cavity, especially in its peripheral region, and has lumps or roughnesses which dig into the bone when the cup is impacted in the cavity.

These lumps or roughnesses are generally not enough, by themselves, to attach the cup in a way which is completely reliable over time. This is why these implants also comprise screws inserted into the bone through the cup to provide additional anchorage.

Some cups also comprise slots, and possibly openings, which give them a certain amount of radial flexibility so that they can be anchored in the acetabular cavity by expanding.

Existing implants which are attached without cement anchor the cup securely and reliably in the acetabulum, but do, however, have the major drawback of allowing debris from the wearing of the material of which the insert is made to diffuse into the acetabular cavity and into the body.

This debris is the result of the rubbing of the head of the femur in the insert and of micro-movements of the insert within the cup. It is also the result of the rubbing of the insert against the somewhat sharp edges which delimit the aforementioned recesses, holes, slots or openings in the cup, this being exacerbated by the fact that the insert tends to creep into these recesses, holes, slots or openings under the effect of the repeat stresses to which the prosthesis is subjected.

Furthermore, the aforementioned holes, slots or openings allow particle-laden synovial fluid to flow towards the bone, this flow being the result of a "pumping effect" caused by the successive application and release of pressure on the implant in the cavity as the patient walks.

This polyethylene debris causes osteolysis, which is detrimental to the firm anchorage of the screws over time, and is not well tolerated by the body.

Another drawback of "press-fit" cups is the risk of an inadequate bond between the external surface of the cup and the ilium, especially at the catching reliefs in the equatorial region of the cup, which means that it is often necessary to use screws for fastening into the bone tissue, even in the case of cups which are coated with a material which assists with osteo-integration, such as calcium hydroxyapatite.

SUMMARY OF THE INVENTION

The present invention aims to overcome these drawbacks by providing an acetabular implant which can be anchored to the innominate bone without cement and without resorting to the fitting of screws.

The implant to which it relates comprises a cup and an insert like the aforementioned, the cup being inserted by impaction and for this purpose, comprising anchoring roughnesses formed on its exterior face.

According to the invention, the cup comprises, formed in its exterior face, coaxial with it, two grooves in the form of helical threads of opposite hand which intersect one another over a large proportion of this external face, which are inclined towards the opening of the cup and which have a depth which increases progressively towards the opening of the cup, these grooves, by intersecting, delimiting a collection of contiguous and imbricated diamond-shaped roughnesses.

Advantageously, these roughnesses are uniformly distributed over the exterior surface of the cup and their dimensions decrease progressively towards the polar region of the cup.

The inclination of these grooves and the increase in their depth along the face of the cup allow the roughnesses to dig progressively into the bone over the entire periphery of the cup, at the time of impacting. At the same time, the number, arrangement and sharp nature of these roughnesses ensure perfect anchorage of the cup in the bone, making the fitting of additional anchoring screws unnecessary.

It is actually on the mechanically strongest part of the natural acetabulum that these roughnesses catch and are the most effective. This is why the depth of the grooves is greatest over that part of the cup which is contiguous with its equatorial plane, opposite which the mechanical strength of the bone wall is highest.

As a consequence of this, the cup is therefore able not to comprise any holes for the passage of such screws, or any slots or openings. The absence of such holes, slots or openings makes it possible to eliminate the risk of creep of the insert and to eliminate any somewhat sharp edge against which the insert may wear away.

The wear on the insert, and therefore the emission of particles, thus remains extremely low in the implant according to the invention.

In addition, the absence of such holes, slots or openings makes it possible for any particles which might be generated by the wearing of the insert to be trapped inside the cup, and therefore makes it possible for the risk of these particles migrating towards the bone, through the cup, to be eliminated.

In a particularly preferred embodiment, the cup has an exterior surface which is treated or coated in such a way as to encourage binding by osteo-integration onto this surface. To achieve this, it receives a coating based on calcium hydroxyapatite. Thanks to a coating with this biomaterial on the external surface of the cup, it becomes possible, after an initial attachment via the mechanical effect of the so-called "press-fit" means to the bony edge of the acitabulum, to achieve a secondary attachment of a physico-chemical nature which strengthens the primary attachment in the first few months after the operation. This attachment is obtained by absorption of the various constituents of the bone tissue onto the calcium hydroxyapatite deposit covering the external face of the cup.

As a preference, the grooves are inclined towards the opening of the cup by an angle of about 45°, for perfect anchorage of the roughnesses in the bone, with no possibility of the said cup springing back out.

Advantageously, the flanks of two roughnesses delimited by one and the same groove are asymmetric, the flank situated on the same side as the opening of the cup being more steeply inclined towards the equatorial plane relative to the axis of the cup than the flank situated on the same side as the closed end of the cup. This asymmetry encourages anchoring.

In actual fact, thanks to this advantageous feature of the invention, the groove flank situated on the same side as the opening has a larger area than the other flank, and this area is not very steeply inclined with respect to the plane tangential to the sphere, which means that the maximum stresses exerted at this point on the bone tissue are mainly compressive stresses, which encourages bone growth and the osteo-integration of the prosthesis in this delicate region.

For the same reason, the threads advantageously, in cross-section, have a "hooked-beak" shape, that is to say have a pointed end edge which is curled down slightly towards the opening of the cup.

It is therefore preferable for the exterior face of the cup to be covered with a coating which encourages osteo-integration, particularly with a coating of calcium hydroxyapatite. The thickness of this coating may, for example, be about 70 to 150μ.

Furthermore, the cup may comprise a hole made at its pole to provide a purchase for an impacting tool, this hole then being tapped and accommodating a threaded obturator which, when fully tightened, lies flush with the internal face of the cup.

This plug makes it possible to eliminate the risk of the insert creeping into the hole and to maintain continuity of the wall of the cup.

In a preferred embodiment of the invention, intended to reduce as far as possible the risk of the formation and propagation of insert debris, the prosthesis may be produced in such a way that:

- the cup has a continuous wall, that is to say has no recesses, holes, slots or openings, and has a polished and perfectly smooth internal surface,
- the hole formed to provide a purchase for the impacting tool is tapped and can accommodate a threaded obturator which, when fully tightened, lies flush with the internal face of the cup, and
- that part of the insert which is intended to fit into the cup has a shape that complements that of the cavity of the cup and comes into close contact with the internal face of the cup.

Thus, the insert matches the smooth and continuous internal face of the cup, and this makes it possible to reduce as far as possible the rubbing and micro-movements of the insert. The absence of recesses, holes, slots or openings in the wall, after the threaded obturator has been fitted, makes it possible to eliminate any somewhat sharp edge against which the insert could wear.

The result of this is that the wear on the insert, and therefore the emission of particles, is extremely low in the implant according to the invention. The large area over which the insert bears against the cup also limits this wear.

Furthermore, the absence of holes, slots or openings makes it possible for any particles to be trapped inside the cup and therefore eliminates the risk of particles migrating, through the cup, towards the bone.

Advantageously, the cavity of the cup has, on the same side as its closed end, a part of perfectly hemispherical shape and, on the same side as its opening, a part of slightly frustoconical shape, these two parts being separated by a conical shoulder, and the insert comprises a hemispherical part, a slightly frustoconical part, and a projection with shapes that correspond respectively to the two parts and to the shoulder of the cavity of the cup.

The two parts of the insert therefore come into close contact with the internal face of the cup when, after the insert has been forcibly fitted into the cavity of the cup, the projection of the insert is locked behind the shoulder of the said cup.

This structure furthermore ensures that the insert is perfectly held in the cup.

According to one embodiment of the insert, it comprises an anti-dislocation rim, and the implant comprises indexing means for angularly positioning this rim with respect to the cup, these indexing means being formed, on the one hand, in a flange that forms part of the insert and, on the other hand, in the edge of the cup delimiting the opening of the cavity.

The anti-dislocation rim may thus be oriented in a way which is appropriate to the specific anatomy of the patient, and the indexing means are outside the cavity of the cup. Any possible emissions of particles generated at these indexing means are thus diffused outside the implant rather than inside, towards the bone.

According to a preferred embodiment of the invention, these indexing means consist of a number of radial notches formed at regular intervals from one another in the periphery of the flange of the insert and of stubs, which can fit into these notches, formed on the equatorial annular face of the cup.

For a good understanding of the invention, it is described again below with reference to the appended diagrammatic drawing which, by way of non-limiting example, depicts one preferred embodiment of the acetabular implant to which it relates.

BRIEF DESCRIPTION OF THE DRAWINGS

FIG. 1 depicts an acetabular implant 1 of a hip prosthesis intended, as shown in FIGS. 4 and 5, to be attached without cement to the innominate bone 2 of the patient, being fitted into the acetabular cavity.

Figure 1:
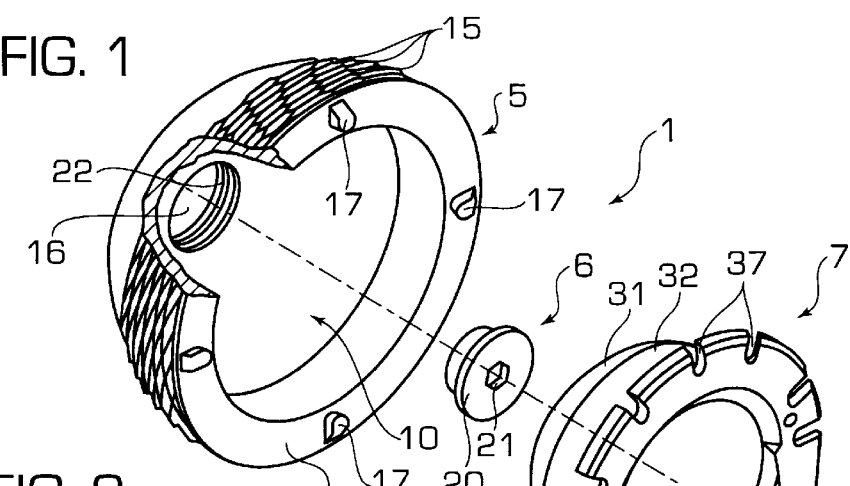
FIG. 1 is a view in exploded perspective of its various constituent parts, with partial cutaway on one part.

The implant 1 consists of a cup 5 made of metal, especially titanium, of a threaded plug 6, made of metal of the same type as the cup 5, and of an insert 7 made of a material which encourages sliding, especially of high-density polyethylene.

The cup 5 has a hemispherical shape and delimits an interior cavity 10 into which the insert 7 can be fitted.

The interior face of the cup 5 has, on the same side as the closed end of this cavity 10, a part 11 of perfectly hemispherical shape and, on the same side as the opening of this cavity 10, a part 12 of slightly frustoconical shape, the smaller circular section of which lies towards the inside of the cavity 10. These two parts 11, 12 are separated by a conical shoulder 13, the smaller section of which lies on the same side as the opening of the cavity 10.

The cup 5 also has an outside diameter which is slightly larger than that of the acetabular cavity and is intended to be anchored in the latter by impacting.

Figure 2:
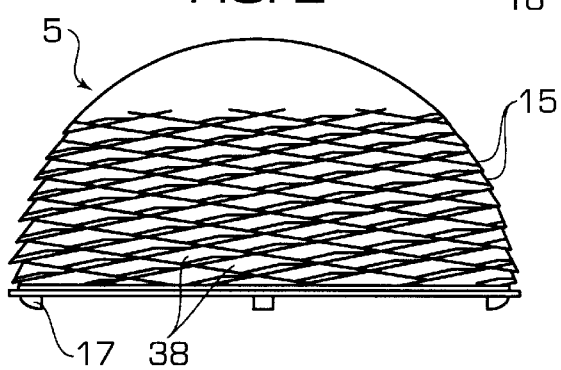
FIG. 2 is a diagrammatic side view of one of these parts.
Figure 3:
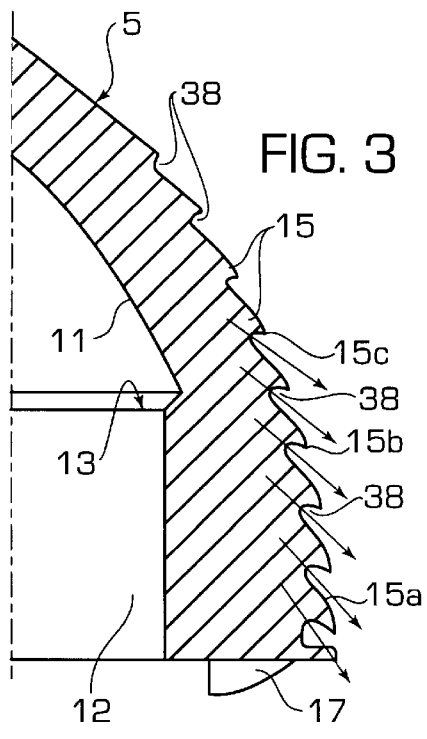
FIG. 3 is a part view on an enlarged scale of the part shown in FIG. 2, in section on the axis of this part.

For this purpose, it comprises, as shown more specifically in FIGS. 1 to 3, a substantial number of contiguous and imbricated diamond-shaped roughnesses 15, which are preferably uniformly distributed.

These roughnesses 15 are formed by the intersection, over a large proportion of the external face of the cup 5, of two grooves 38 in the form of helical threads of opposite hand formed coaxially to the cup 5. It can be seen in FIG. 3 that these grooves 38 are inclined towards the opening of the cup 5 by an angle of about 45°, that their depth increases progressively towards this opening, and that the flanks 15a, 15b, of two roughnesses 15, delimited by one and the same groove 38 are asymmetric, the flank 15a situated on the same side as the opening of the cup 5 being more steeply inclined relative to the axis of the cap 5, and therefore nearer to the plane tangential to the sphere at this point, than the flank 15b situated on the same side as the closed end of the cup 5.

The threads in cross-section have a "hooked-beak" shape, that is to say comprise a sharp end edge 15c which is curled down slightly towards the opening of the cup 5.

The external surface of the cup, including the flanks 15a of the threads, is coated with a layer of calcium hydroxyapatite, by any technique well known to those skilled in the art in the field of metal prostheses intended for osteo-integration, for example using the APS (atmospheric plasma spraying) method which employs a plasma torch.

The cup 5 also comprises a tapped hole 16 formed at its pole to provide a purchase for the impacting tool, and four stubs 17 formed at equal distances apart on its equatorial annular face 18 delimiting the opening of the cavity 10.

Figure 4:
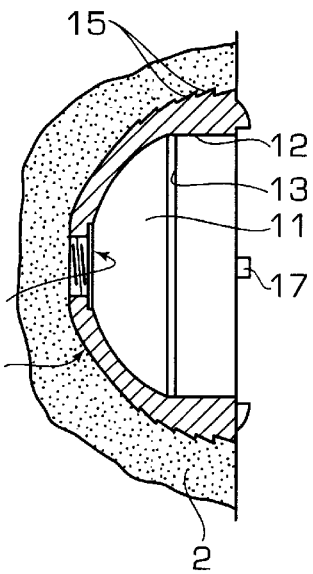
FIG. 4 is a view of this same part after implantation, in section on the axis of this element.

The threaded plug 6 is shaped so that it can be screwed into the hole 16. It has an annular head 20 in which a hexagon socket 21 is formed, so that it can be turned and tightened using an appropriate key. This head 20 fits, when fully tightened, into an annular recess 22 coaxial with the hole 16 and therefore, as shown in FIG. 4, lies flush with the internal face of the cup 5.

The insert 7 delimits a spherical cavity 30 intended to accommodate, with the possibility of pivoting, the corresponding spherical head (not depicted) of a femoral shaft, so as to allow the prosthetic joint to work.

It comprises a hemispherical part 31, a slightly frusto-conical part 32 and a projection 33 with shapes that correspond respectively to the parts 11, 12 and to the shoulder 13 of the cavity 10. These parts 31 and 32 also come into close contact with the internal face of the cup 5 when, after the insert 7 has been forcibly fitted into the cavity 10, the projection 33 is locked behind the shoulder 13.

Figure 5:
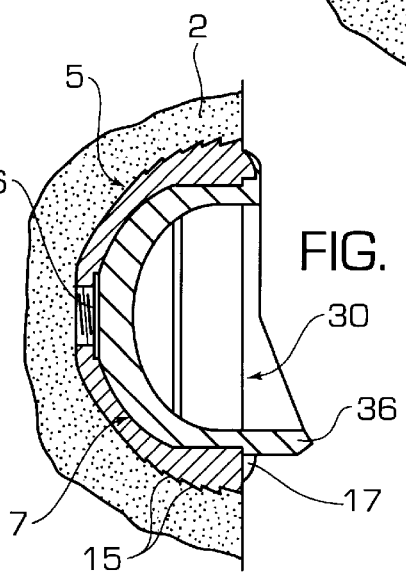
FIG. 5 is a view of the implant after fitting, in section on the axis of this implant.

Furthermore, the insert 7 comprises a flange 35, which, as shown by FIG. 5, comes into contact with the face 18 when the inset 7 is locked into the cavity 10.

This flange 35 comprises a rim 36 that prevents the femoral head from dislocating and has a number of radial notches 37 formed at regular distances apart in its periphery. These notches can fit around studs 17.

In practice, the cup 5 is mounted on the rod of an impacting instrument (not depicted) and is then impacted into the acetabular cavity of the innominate bone 2 so that its roughnesses 15 dig into the bone wall.

During this impacting, the roughnesses 15 dig progressively into the bone over the entire periphery of the cup 5.

The number, shape, arrangement and sharp nature of these roughnesses 15 ensure perfect anchorage of the cup 5 in the bone, without it being possible for the cup to spring back out.

That the cup 5 has indeed come into contact with the bottom of the cavity can be verified using the hole 16, after the impacting tool has been withdrawn.

The plug 6 is then screwed into the hole 16, then the insert 7 is partially fitted into the cavity 10 and is angularly positioned with respect to the cup 5 so that the rim 36 is oriented in the most suitable way given the specific anatomy of the patient. Once this positioning has been carried out, the insert 7 is forcibly fitted into the cavity 10 until its projection 33 locks behind the shoulder 13.

The absence of holes, slots or openings in the wall of the cup 5, once the plug 6 has been fitted, eliminates the risk of the insert 7 creeping and eliminates any somewhat sharp edge against which this insert could creep. Furthermore, the insert 7 closely matches the smooth and continuous internal face of the cup 5.

This means that the rubbing and micro-movements of the insert 7 with respect to the cup 5 are reduced as far as possible and that the emission of wear particles is extremely low.

Any wear particles that there might be are trapped inside the cup 5, and this eliminates the risk of these particles migrating, through the cup 5, towards the bone.

Furthermore, any particles that might be generated at the notches 37 are diffused out of the implant 1, rather than towards the bone.

The osteo-integration bond, which begins a few weeks after fitting, becomes effective in a few months to one year.

What is claimed is:

1. An acetabular implant, attachable without cement, comprising:

a cup (5) of hemispherical shape with a circular open base and a pole, delimiting an internal cavity (10); and an insert (7) that can be fitted into said cavity (10), the cup (5) being fitted by impacting and, for this purpose, comprising anchoring roughnesses (15), formed on its exterior face, which have a diamond shape and are contiguous and imbricated;

wherein the cup (5) comprises, formed in its exterior face and coaxial with it, two grooves, in the form of helical threads (38) of opposite hand, which intersect one another over a large proportion of said external face, which are inclined towards the base of the cup (5) and which have a depth which increases progressively towards the base of the cup (5), said grooves, by intersecting, delimiting a large number of said roughnesses (15).

2. Acetabular implant according to claim 1, characterized in that the grooves (38) are inclined towards the base of the cup (5) by an angle of about 45°.

3. Acetabular implant according to claim 1, characterized in that flanks (15a, 15b) of two roughnesses (15) delimited by one and the same groove (38) are asymmetric, the flank (15a) situated on the same side as the base of the cup (5) being more steeply inclined relative to the axis of the cup (5) than the flank (15b) situated on the same side as the pole of the cup (5).

4. Acetabular implant according to claim 1, characterized in that the threads (38), in cross-section, have a "hooked-beak" shape, that is to say have a pointed end edge (15a) which is curled down slightly towards the base of the cup (5).

5. Implant according to claim 1, characterized in that the roughnesses (15) are uniformly distributed over the exterior surface of the cup (5), and their dimensions decrease progressively towards the polar region of the cup.

6. The acetabular implant according to claim 1, characterized in that the exterior face of the cup (5) is covered with a coating of calcium hydroxyapatite that encourages osteointegration.

7. Acetabular implant according to claim 1, characterized in that the cup (5) comprises a hole (16) made at its pole to provide a purchase for an impacting tool, this hole (16) being tapped and accommodating a threaded obturator (6) which, when fully tightened, lies flush with the internal face of the cup (5).

8. Acetablular implant according to claim 1, characterized in that;

the cup (5) has a continuous wall, that is to say has no recesses, holes, slots or openings, and has a polished and perfectly smooth internal surface, a hole (16) formed to provide a purchase for an impacting tool is tapped and can accommodate a threaded plug (6) which, when fully tightened, lies flush with the internal surface of the cup (5), and that part (31, 32, 33) of the insert (7) which is intended to fit into the cup (5) has a shape that complements that of the cavity (10) of the cup (5) and comes into close contact with the internal surface of the cup (5).

9. Acetabular implant according to claim 1, characterized in that it comprises an insert (7) which has an anti-dislocation rim (36), and in that it comprises indexing means (17, 37) for angularly positioning this rim (36) with respect to the cup (5), these indexing means (17, 37) being formed, on the one hand, in a flange (35) that forms part of the insert (7) and, on the other hand, in a surface (18) of the cup (5) delimiting an opening of the cavity (10).

10. Acetabular implant according to claim 9, characterized in that the indexing means consist of a number of radial notches (37) formed at regular intervals from one another in the periphery of the flange (35) and of stubs (17), which can fit into these notches (37), formed on the equatorial annular face (18) of the cup (5).

11. Acetablular implant according to claim 1, characterized in that the cavity (10) of the cup (5) has, on the same side as its closed end, a part (11) of perfectly hemispherical shape and, on the same side as its opening, a part (12) of slightly frustoconical shape, these two parts (11, 12) being separated by a conical shoulder (13), and in that the insert (7) comprises a hemispherical part (31), a slightly frustoconical part (32), and a projection (33) with shapes that correspond respectively to the two parts (11, 12) and to the shoulder (13) of the cavity (10) of the cup (5).

12. The acetabular implant according to claim 8, wherein the grooves (38) are inclined towards the base of the cup (5) by an angle of about 45°;

flanks (15a, 15b) of two roughnesses (15) delimited by one and the same groove (38) are asymmetric, the flank (15a) situated on the same side as the base of the cup (5) being more steeply inclined relative to the axis of the cup (5) than the flank (15b) situated on the same side as the pole of the cup (5);

wherein the threads (38), in cross-section, have a "hooked-beak" shape, that is to say have a pointed end edge (15a) which is curled down slightly towards the base of the cup (5); and wherein the roughnesses (15) are uniformly distributed over the exterior surface of the cup (5), and their dimensions decrease progressively towards the polar region of the cup.

* * * * *